United States Patent
Höök et al.

(10) Patent No.: US 7,094,880 B2
(45) Date of Patent: Aug. 22, 2006

(54) DECORIN PROTEOGLYCAN INHIBITOR OF FIBRINOGEN BLOOD CLOTTING

(75) Inventors: Magnus Höök, Houston, TX (US); Tracey A. Dugan, Houston, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 10/898,841

(22) Filed: Jul. 26, 2004

(65) Prior Publication Data

US 2005/0020491 A1 Jan. 27, 2005

Related U.S. Application Data

(60) Provisional application No. 60/490,081, filed on Jul. 25, 2003, now abandoned.

(51) Int. Cl.
*C07K 1/00* (2006.01)
*C07K 14/00* (2006.01)
*C07K 17/00* (2006.01)

(52) U.S. Cl. ..................................... 530/350
(58) Field of Classification Search ................ 530/350; 514/12

See application file for complete search history.

(56) References Cited

U.S. PATENT DOCUMENTS

2003/0148351 A1* 8/2003 Henry et al. .................... 435/6

OTHER PUBLICATIONS

Seidler et al., Core protein dependence of epimerization of glucuronosyl residues in galactosaminoglycans, J. Biol. Chem., (2002), 277(44), p. 42409-42416.*
Oldberg et al., Amino terminal deletions in the decorin core protein leads to the biosynthesis of proteoglycans with shorter glycosaminoglycan chains, FEBS Letters, (1996), 386, p. 29-32.*
Hauser et al., Different galactosaminoglycan composition of small proteoglycans from osteosarcoma cells, Glycobiology, (1993), 3(6), p. 557-562.*

* cited by examiner

*Primary Examiner*—Karen Cochrane Carlson
*Assistant Examiner*—Agnes B. Rooke
(74) *Attorney, Agent, or Firm*—Benjamin Aaron Adler

(57) ABSTRACT

The present invention provides compositions and methods of inhibiting fibrin(ogen) clot formation by utilizing decorin proteoglycan as an anticoagulating and antithrombotic agent. The decorin proteoglycan comprises a decorin core protein or a fragment thereof covalently linked to a galactosaminoglycan polysaccharide. The decorin core protein acts as an anticoagulant and as a carrier for the delivery of an antithrombotic galactosaminoglycan to fibrinogen. Fibrin clotting is inhibited by the decorin proteoglycan in a concentration-dependent fashion.

8 Claims, 6 Drawing Sheets

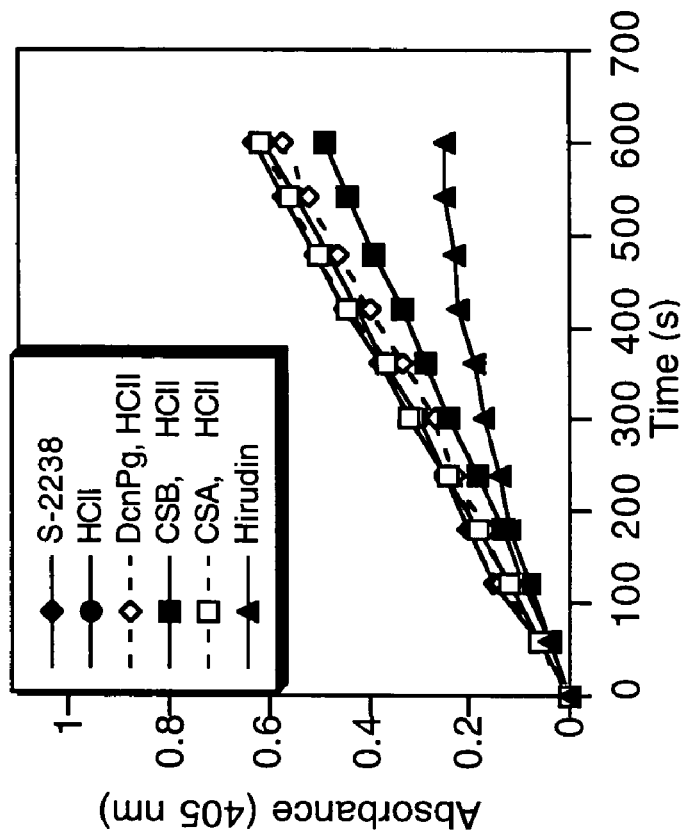
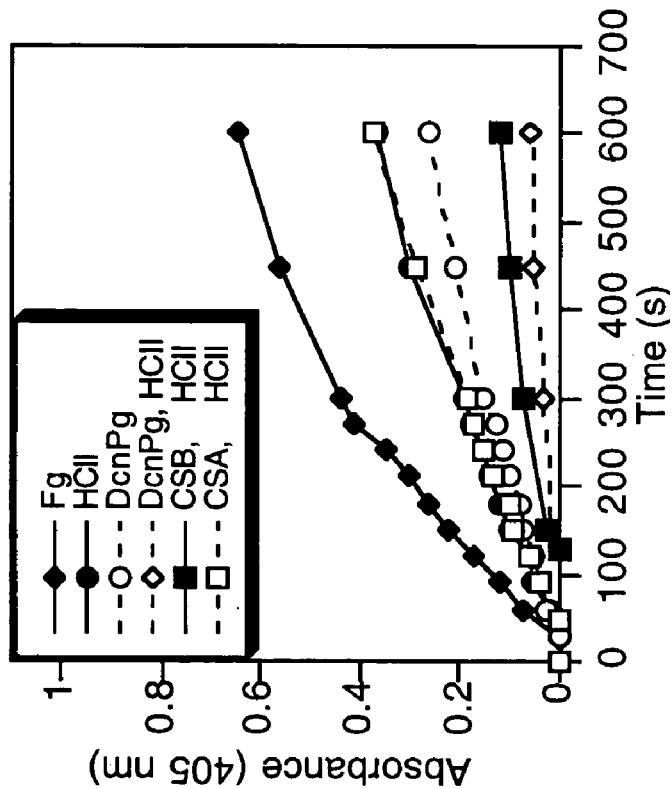
Fig. 3A
Fig. 3B

DECORIN PROTEOGLYCAN INHIBITOR OF FIBRINOGEN BLOOD CLOTTING

CROSS REFERENCE TO RELATED APPLICATION

This non-provisional patent application claims benefit of provisional patent application U.S.S.N. No. 60/490,081, filed Jul. 25, 2003, now abandoned.

FEDERAL FUNDING LEGEND

This invention was produced in part using funds obtained through a National Institutes of Health grant AR42919. Consequently, the federal government has certain rights in this invention.

BACKGROUND OF THE INVENTION

1. Field of the Invention

The present invention relates generally to the field of blood clotting research. More specifically, the present invention provides methods of using decorin proteoglycan as an anticoagulating and/or antithrombotic agent to inhibit fibrin (ogen) clot formation.

2. Description of the Related Art

Decorin is composed of a 40 kDa core protein and a glycosaminoglycan chain. Many glycosaminoglycans affect blood coagulation activity. For example, heparin and heparan sulfate have been used as efficient anticoagulants clinically for decades. These polysaccharides indirectly inhibit thrombin by activating serpins. Heparin activates antithrombin III, the major physiological regulator of thrombin, as well as heparin cofactor II. Both heparin-induced thrombocytopenia and hemorrhage are side effects to the use of heparin as an antithrombotic agent.

Although heparin/antithrombin III complexes efficiently inhibit soluble thrombin, they only weakly inhibit thrombin bound to surfaces such as membranes or a fibrin(ogen) clot. Fibrin-bound thrombin represents a reservoir of active thrombin that can exacerbate both venous and arterial thrombosis by generating more fibrin locally or when released by fibrinolysis. Fibrin-bound thrombin may also activate factor XIII, the transglutaminase that crosslinks fibrin and thrombin-activatable fibrinolysis inhibitor.

Fibrin-bound thrombin is inaccessible to heparin/heparin cofactor II inactivation, but it is susceptible to dermatan sulfate/heparin cofactor II inactivation. As opposed to heparin, dermatan sulfate specifically activates heparin cofactor II inhibition of thrombin. However, hemorrhage is also a side effect of utilizing dermatan sulfate as an antithrombotic agent.

Accordingly, there is a need in the art for anticoagulating and antithrombotic agents with high activity and low incidents of side effects. The present invention fulfills this longstanding need.

SUMMARY OF THE INVENTION

The present invention provides compositions and methods of utilizing decorin proteoglycan to inhibit thrombin-induced fibrin(ogen) clotting. Antithrombotic dermatan sulfate or dermatan sulfate/heparin cofactor II complex is specifically targeted to fibrin(ogen), an important site of thrombin action and a reservoir of active thrombin.

The anticoagulating and antithrombotic decorin proteoglycan of the present invention comprise (i) a decorin core protein or a fragment thereof and (ii) a galactosaminoglycan polysaccharide. In one embodiment, the decorin core protein or a fragment thereof is covalently linked to the galactosaminoglycan polysaccharide. In one specific embodiment, the decorin core protein fragment comprises the N-terminus of the decorin core protein. According to one particular embodiment, the decorin-core protein fragment is a 45 amino acid residue recombinant $Zn^{2+}$-binding peptide (SEQ ID NO: 2) mimicking the N-terminal segment of decorin (SEQ ID NO: 1). Examples of galactosaminoglycan polysaccharides include heparin, heparin sulfate, dermatan sulfate, chondroitin sulfate, or a mixture these galactosaminoglycan polysaccharides.

In another embodiment, there is provided an anticoagulating and antithrombotic composition comprising the decorin proteoglycan disclosed herein and a pharmaceutically acceptable carrier. This anticoagulating and antithrombotic composition can be incorporated into a kit for inhibiting fibrin clot formation.

In yet another embodiment, there is provided a method of inhibiting fibrin clot formation, comprising the step of contacting fibrinogen with the decorin proteoglycan disclosed herein. In one embodiment, the decorin proteoglycan is attached to the surface of a medical device or a polymeric biomaterial.

In yet another embodiment, there is provided a method of inhibiting fibrin clot formation in a subject such as an animal or a human, comprising the step of administering the decorin proteoglycan disclosed herein to said subject.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIGS. 3A–B show the comparison of inhibitory action of decorin proteoglycan and heparin cofactor II towards thrombin cleavage of fibrinogen or a chromogenic substrate. Two μM fibrinogen was pre-incubated in HBS, 0.1% CHAPS, 20 μM $ZnSO_4$ with or without 2.5 U/ml heparin cofactor II (HCII); 0.4 μM decorin proteoglycan (DcnPg) expressed by mammalian cells capable of producing dermatan sulfate; 0.4 μM decorin proteoglycan plus 2.5 U/ml heparin cofactor II; 0.4 μM chondroitin sulfate B (CSB) plus 2.5 U/ml HCII; 0.4

µM chondroitin sulfate A (CSA) plus 2.5 U/ml HCII (FIG. 3A); or 2.5 U/ml hirudin or 0.6 mM chromogenic thrombin substrate S-2238 (FIG. 3B). After adding thrombin to 0.25 U/ml, the progress of each reaction was traced by the absorbance at 405 nm which detects fibrin clotting (FIG. 3A) or p-nitroaniline release (FIG. 3B).

Figure 4:
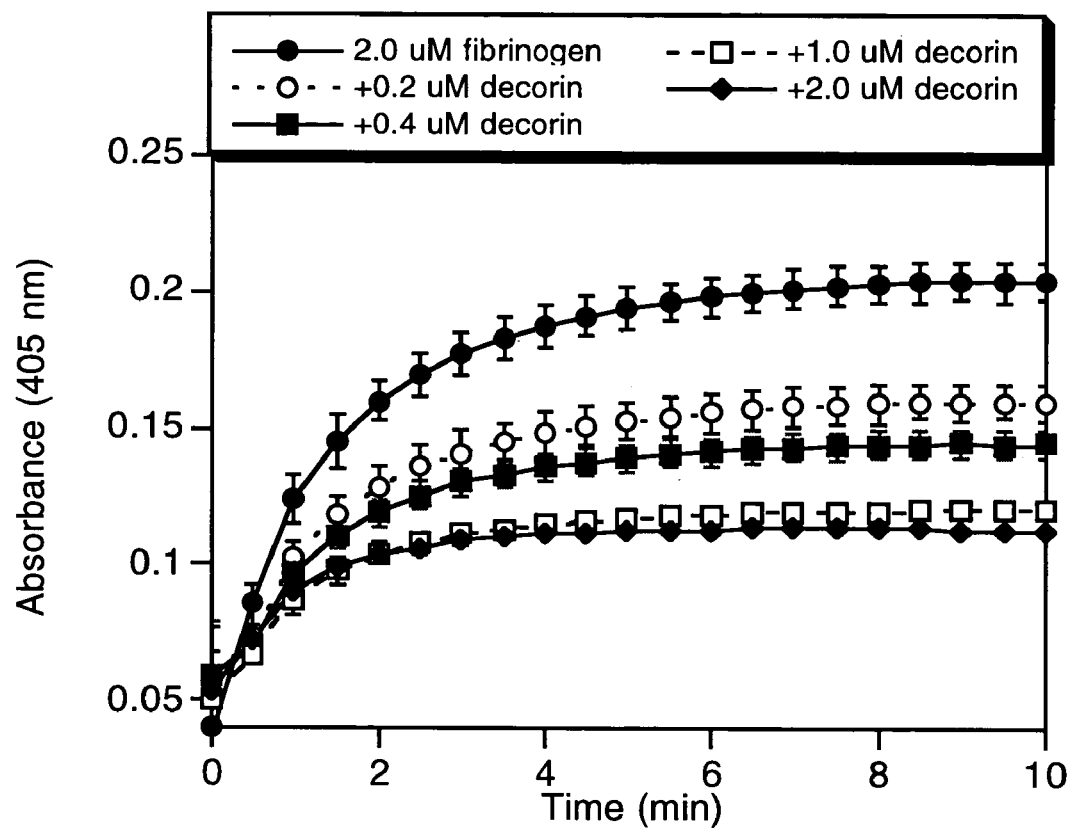

FIG. 4 shows the concentration-dependent effects of decorin core protein (decorin) on fibrin clotting. Two µM fibrinogen was pre-incubated for 1.5 hours at ambient temperature in HBS, 0.1% CHAPS, 20 µM $ZnCl_2$, 5 mM $CaCl_2$, 5 mM EACA, pH 7.4 with or without increasing concentrations of decorin core protein (decorin) expressed by CH0745 cells. All subsequent steps were performed as described above.

Figure 5C:
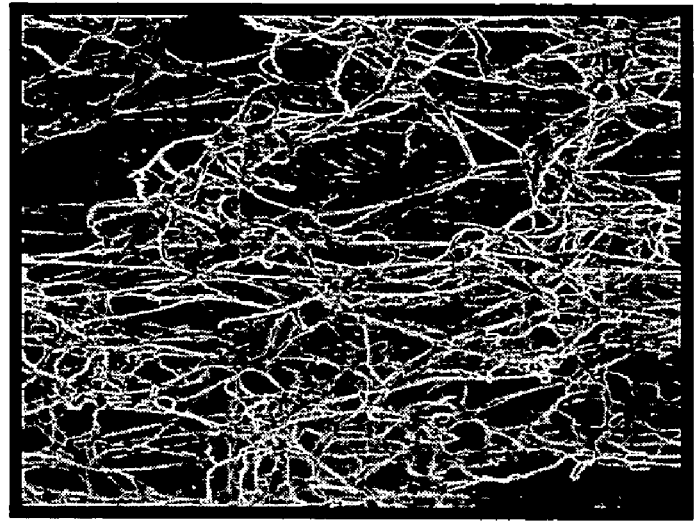
Figure 5B:
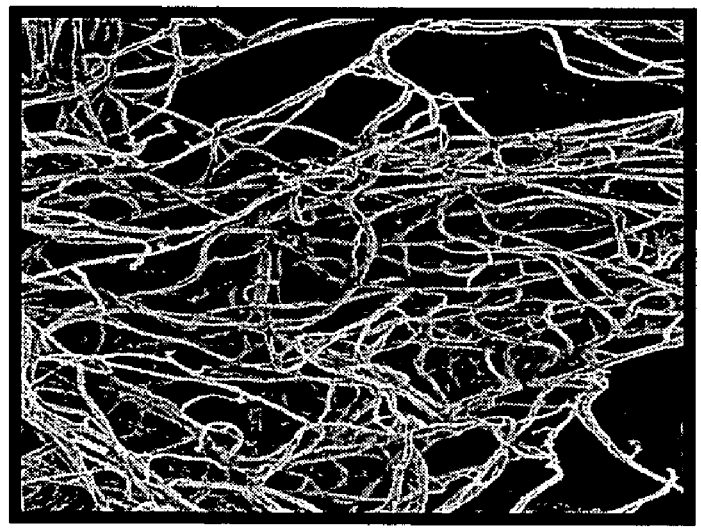
Figure 5A:
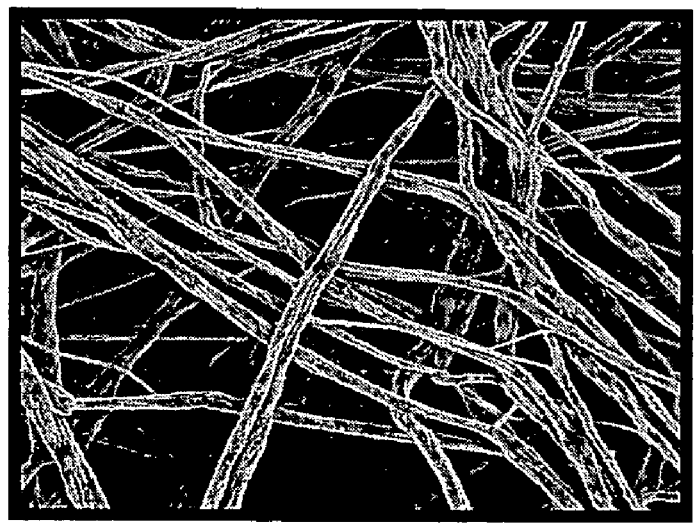

FIGS. 5A–C show decorin core protein alters the structure of a fibrin(ogen) clot. Fibrin(ogen) clotting was induced by the addition of thrombin (final concentration 0.4 U/ml) to fibrinogen pre-incubated in the absence or presence of decorin core protein under the solution conditions described in FIG. 4. Scanning electron microscopy was utilized to obtain images of clots formed from 1.2 µM fibrin(ogen) alone (FIG. 5A) or in the presence of 0.24 µM (FIG. 5B) or 1.2 µM (FIG. 5C) decorin core protein. (16,000X magnification).

Figure 6:
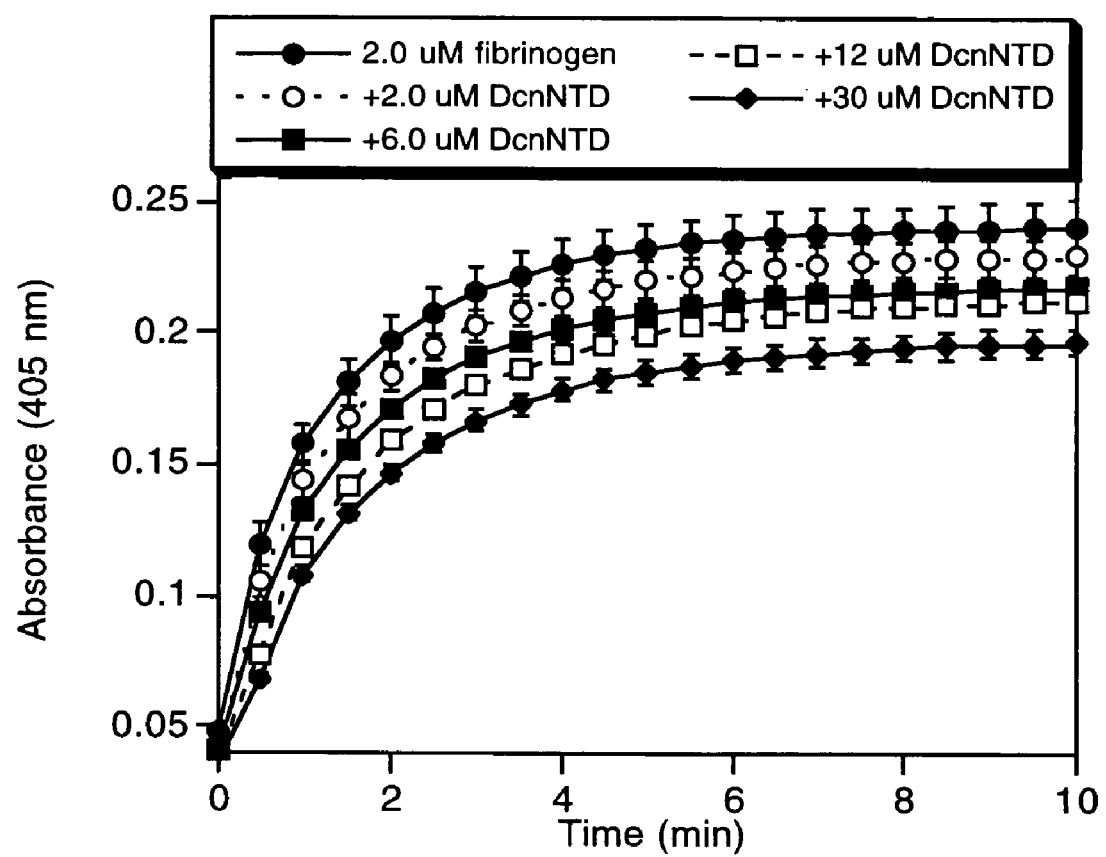

FIG. 6 shows the concentration-dependent effects of a 45 amino acid residue peptide mimetic of the N-terminal region of decorin core protein (DcnNTD) on fibrin clotting. Clotting assays were performed as described above in FIG. 4.

DETAILED DESCRIPTION OF THE INVENTION

The present invention provides a method of inhibiting fibrin(ogen) clot formation by utilizing decorin proteoglycan as an anticoagulating and antithrombotic agent. In one embodiment, decorin proteoglycan consists of decorin core protein and a covalently attached antithrombotic galactosaminoglycan polysaccharide. A method of inhibiting fibrin clotting using decorin core protein, or related peptides, which act as an anticoagulating agents has been described in U.S. Pat. No. 6,413,93.1, the entire content of which is incorporated herein by reference. Likewise, dermatan sulfate polysaccharide has been utilized as an effective antithrombotic agent both in vivo and in vitro. Decorin proteoglycan of the present invention, which is a combination of decorin core protein and an attached antithrombotic galactosaminoglycan polysaccharide, is an improvement over either decorin core protein or dermatan sulfate alone.

Features that contribute to the mode of action of the present decorin proteoglycan derive from each structural component and include: 1) the fibrinogen-binding structure of the decorin core protein and 2) the galactosaminoglycan composition of the polysaccharide. Decorin-fibrinogen binding is mediated by the N-terminal segment of the core protein, a segment that forms multimers in the presence of zinc (Dugan et al., 2003). The N-terminal segment of decorin core protein binds zinc at physiological concentrations (Yang et al., 1999). Furthermore, both decorin proteoglycan and decorin core protein slow the progress of fibrin clotting in a zinc-dependent fashion and at physiological zinc concentrations.

The galactosaminoglycan component of decorin proteoglycan may consist of chondroitin sulfate or dermatan sulfate, or a mixture thereof, depending upon the cell-type in which it is expressed. Acting alone, chondroitin sulfate polysaccharide promotes fibrin clotting, while dermatan sulfate polysaccharide indirectly inhibits thrombin through heparin cofactor II activation. Dermatan sulfate-containing galactosaminoglycans isolated from decorin as well as type V collagen-bound decorin proteoglycan enhance the inhibitory activity of heparin cofactor II toward thrombin cleavage of a chromogenic substrate. Decorin proteoglycan according to the present invention enhances heparin cofactor II inhibition of thrombin-induced fibrin(ogen) clotting. Significantly, decorin proteoglycan is a more potent enhancer than dermatan sulfate polysaccharide. Accordingly, decorin proteoglycan produced in HEK 293 cells contains an antithrombotic component. Taken together, the decorin core protein acts as an anticoagulant and as a carrier for the delivery of an antithrombotic galactosaminoglycan to fibrinogen.

The present invention provides several methods and related biological compositions involved in the inhibition of fibrin(ogen) clot formation. The invention provides a method of inhibiting fibrin clot formation, comprising contacting fibrinogen with a decorin proteoglycan composition. As used herein, the term "inhibiting clot formation" refers to any prolonging in the time of clot formation or any reduction in the extent of clot formation as compared to control conditions in the absence of decorin proteoglycan composition.

In one aspect of the present invention, there is provided an anticoagulating and antithrombotic decorin proteoglycan comprising decorin core protein or a fragment thereof and a galactosaminoglycan polysaccharide. In one embodiment, the decorin core protein or a fragment thereof is covalently linked to the galactosaminoglycan polysaccharide. Preferably, the decorin core protein or a fragment thereof comprises a fibrinogen-binding domain. In general, the decorin core protein fragment comprises the N-terminus (SEQ ID NO: 1), or fragments or derivatives of SEQ ID NO: 1, of the decorin core protein. In one embodiment, the decorin core protein fragment has the sequence of SEQ ID NO: 2 or fragments or derivatives thereof. Representative examples of galactosaminoglycan polysaccharides contained in the present decorin proteoglycan include heparin, heparin sulfate, chondroitin sulfate, dermatan sulfate, or mixtures of these or other galactosaminoglycan polysaccharides.

The present invention also provides a kit for inhibiting fibrin clot formation, comprising the present decorin proteoglycan which is dispersed in a pharmaceutically acceptable carrier.

In another embodiment, there is provided a method of inhibiting fibrin clot formation, comprising the step of contacting fibrinogen with a decorin proteoglycan composition effective to inhibit fibrin clot formation in a sample. In general, the fibrin clot formation takes place in a biological sample such as a blood sample. In another embodiment, the decorin proteoglycan is attached to the surface of a medical device or a polymeric biomaterial.

In yet another embodiment, there is provided a method of inhibiting fibrin clot formation in a subject such as an animal or a human, comprising the step of providing to the subject a decorin proteoglycan composition effective to inhibit fibrin clot formation.

In one embodiment, the decorin proteoglycan is attached to the surface of a medical device or a polymeric biomaterial.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

The amino acids described herein are preferred to be in the "L" isomeric form. However, residues in the "D" isomeric form can be substituted for any L-amino acid residue, as long as the desired functional property of immunoglobulin binding is retained by the polypeptide. NH2 refers to the free amino group present at the amino terminus of a polypeptide. COOH refers to the free carboxy group present at the carboxy terminus of a polypeptide. In keeping with standard polypeptide nomenclature, *J Biol. Chem.*, 243: 3552–59 (1969), abbreviations for amino acid residues are known in the art.

Nonstandard amino acids may be incorporated into proteins by chemical modification of existing amino acids or by de novo synthesis of a protein/peptide. A Nonstandard amino acid refers to an amino acid that differs in chemical structure from the twenty standard amino acids encoded by the genetic code. Post-translational modification in vivo can also lead to the presence of a nonstandard or amino acid derivative in a protein. The N-terminal $NH_2$ and C-terminal COOH groups of a protein can also be modified, for example, by natural or artificial post-translational modification of a protein.

Proteins/peptides, such as the decorin core protein or fragments thereof, may be modified by amino acids substitutions. Often, some changes result in significant changes in the activity (agonists versus antagonists) and potency/affinity of proteins/peptides while others have little or no effect. Conservative substitutions are least likely to drastically alter the activity of a protein. A "conservative amino acid substitution" refers to replacement of amino acid with a chemically similar amino acid, i.e. replacing nonpolar amino acids with other nonpolar amino acids; substitution of polar amino acids with other polar amino acids, acidic residues with other acidic amino acids, etc. Examples of preferred conservative substitutions are set forth in Table I:

TABLE 1

Conservative Amino Acid Substitutions

| Original Residue | Preferred Conservative Substitutions | Most Preferred Conservative Substitution |
|---|---|---|
| Ala (A) | Val; Leu; Ile | Val |
| Arg (R) | Lys; Gln; Asn | Lys |
| Asn (N) | Gln; His; Lys; Arg, Ser | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala, DAla | Pro |
| His (H) | Asn; Gln; Lys; Arg | Arg |
| Ile (I) | Leu; Val; Met; Ala; Phe; Nle | Leu |
| Leu (L) | Ile; Val; Met; Ala; Phe; Nle | Ile |
| Lys (K) | Arg; Gln; Asn | Arg |
| Met (M) | Leu; Phe; Ile, Nle | Leu |
| Phe (F) | Leu; Val; Ile; Ala | Leu |
| Pro (P) | Gly, Sar | Gly |
| Ser (S) | Thr | Thr |
| Thr (T) | Ser | Ser |
| Trp (W) | Tyr, Nal, Cpa | Tyr |
| Tyr (Y) | Trp; Phe; Thr; Ser, His | Phe |
| Val (V) | Ile; Leu; Met; Phe; Ala; Nle | Leu |

Sar = sarcasine,
Nal = naphthylalanine,
Cpa = 4-chloro-phenylalanine

"Chemical derivative" refers to a subject polypeptide, such as the decorin core protein or fragments thereof, having one or more residues chemically derivatized by reaction of a functional side group. Such derivatized polypeptides include, for example, those in which free amino groups have been derivatized to form specific salts or derivatized by alkylation and/or acylation, p-toluene sulfonyl groups, carbobenzoxy groups, t-butylocycarbonyl groups, chloroacetyl groups, formyl or acetyl groups among others. Free carboxyl groups may be derivatized to form organic or inorganic salts, methyl and ethyl esters or other types of esters or hydrazides and preferably amides (primary or secondary). Chemical derivatives may include those peptides which contain one or more naturally occurring amino acids derivatives of the twenty standard amino acids. For example, 4-hydroxyproline may be substituted for serine; and ornithine may be substituted for lysine. Peptides embraced by the present invention also include peptides having one or more residue additions and/or deletions relative to the specific peptide whose sequence is shown herein, so long as the modified peptide maintains the requisite biological activity.

The preferred dose for human administration can be determined based on the needs of the individual patient and the nature of the disorder being treated. The dose should be adjusted to suit the individual to whom the composition is administered and will vary with age, weight and metabolism of the individual. In general, decorin proteoglycan is administered in a dosage range of from about 0.01 mg/kg to about 100 mg/kg of the individual's body weight.

Suitable methods of administration of any pharmaceutical composition disclosed in this application include, but are not limited to, topical, oral, intravenous, and intraperitoneal administration.

For topical administration, the composition can be formulated in the form of an ointment, cream, gel, or lotion. Wound or surgical dressings, or sutures may be impregnated with the composition. The composition may contain conventional additives, such as preservatives or solvents to promote penetration and emollients. Topical formulations may also contain conventional carriers such as cream or ointment bases, ethanol, or oleyl alcohol.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Concentration-Dependent Effect of Decorin Proteoglycan On The Progress of Fibrin Clotting Two µM fibrinogen was pre-incubated alone for 4 hours at ambient temperature in HBS, 0.1% CHAPS, 20 µM ZnSO$_4$ or with increasing concentrations of decorin proteoglycan derived from transfected mammalian cells. Subsequently, aliquots of each pre-incubation mixture were dispensed into a microliter plate. Clotting was initiated by the addition of thrombin to a final concentration of 0.25 U/ml and monitored by absorbance at 405 nm.

Figure 1:
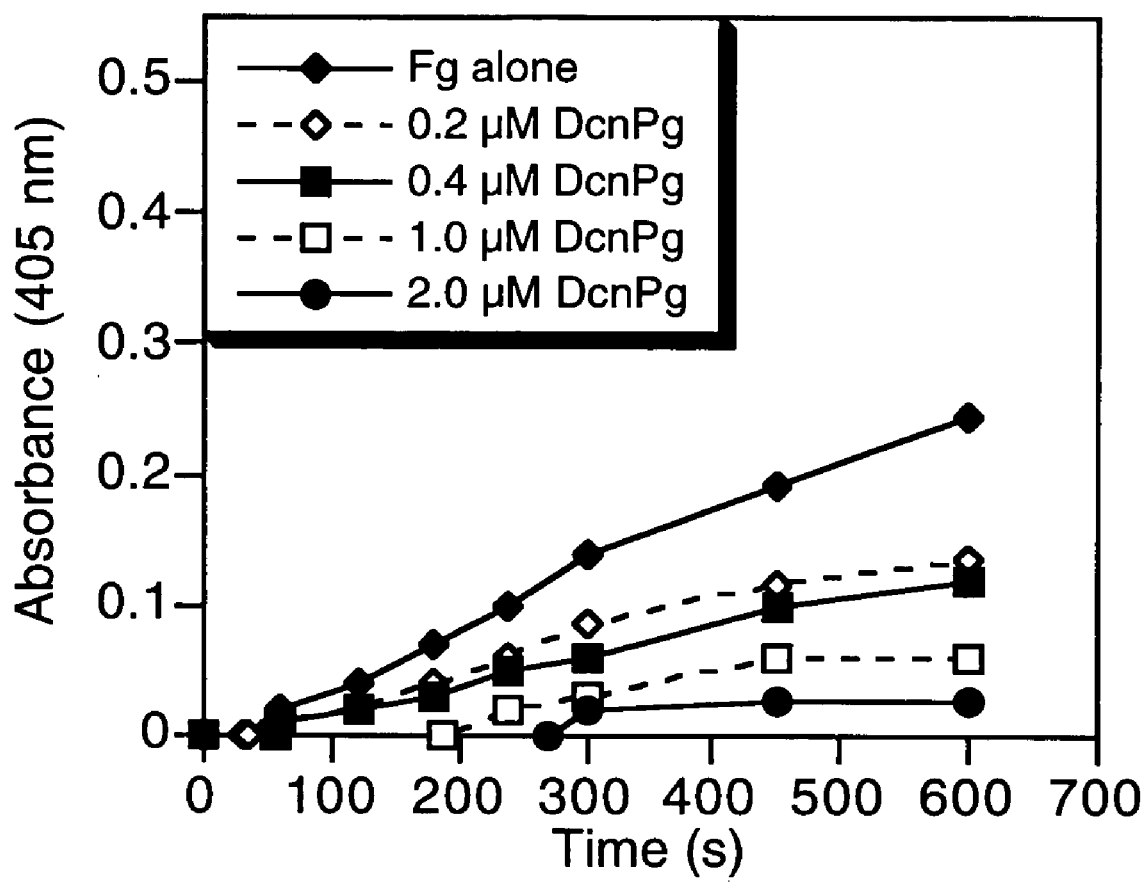
FIG. 1 shows the concentration-dependent effects of decorin on the progress of fibrin clotting. Two μM fibrinogen (Fg) was pre-incubated alone for 4 hours at ambient temperature in HBS, 0.1% CHAPS, 20 μM $ZnSO_4$ or with increasing concentrations of decorin proteoglycan (DcnPg). Clotting was initiated by the addition of thrombin to a final concentration of 0.25 U/ml and monitored by absorbance at 405 nm. This example shows that contacting fibrinogen with increasing concentrations of decorin proteoglycan prior to introducing thrombin slows the progress of fibrin clotting in a concentration-dependent fashion.

FIG. 1 shows that contacting fibrinogen with increasing concentrations of decorin proteoglycan prior to introducing thrombin slows the progress of fibrin clotting in a concentration-dependent fashion.

EXAMPLE 2

Zn$^{2+}$-Dependent Effect of Decorin Proteoglycan On Fibrin Clotting

Figure 2B:
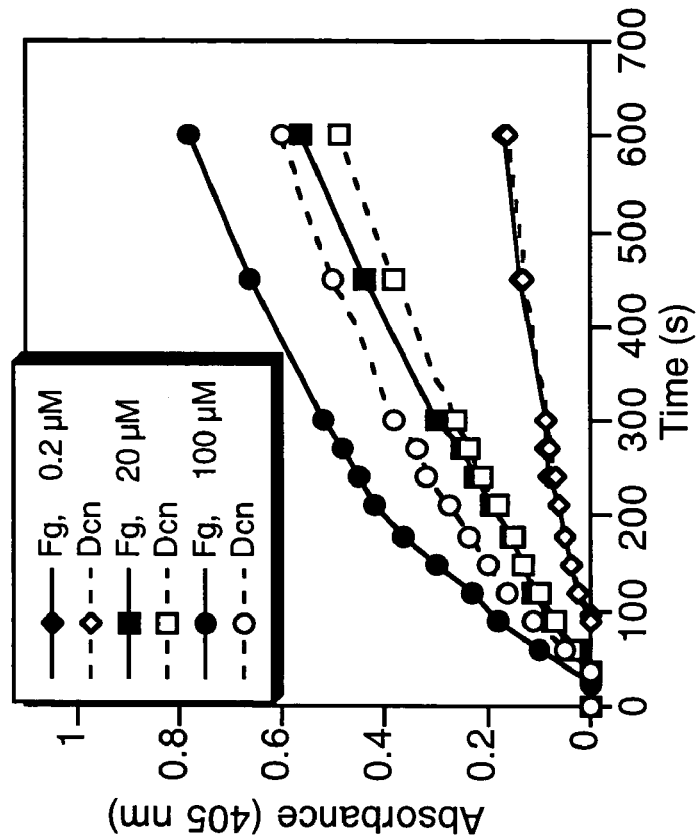
FIGS. 2A–B show $Zn^{2+}$-dependent effect of decorin on fibrin clotting. Two μM fibrinogen was pre-incubated in HBS, 0.1% CHAPS containing either 0.2 μM, 20 μM, or 100 μM $ZnSO_4$. Decorin proteoglycan (DcnPg) (0.4 μM) derived from cultured mammalian cells (FIG. 2A), or 2 μM decorin core protein (Dcn) expressed by vaccinia virus-infected mammalian cell line CH0745 that lacks xylosyl transferase activity (FIG. 2B) were also added to the medium. Time course of fibrin clotting was monitored spectroscopically after adding thrombin to a final concentration of 0.25 U/ml.
Figure 2A:
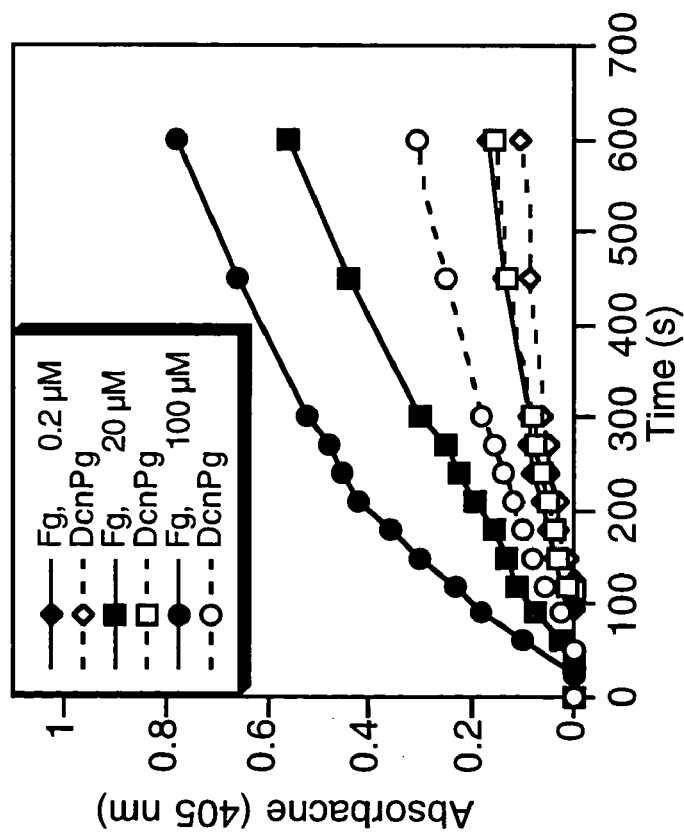

Two μM fibrinogen was pre-incubated in HBS, 0.1% CHAPS containing either 0.2 μM, 20 μM, or 100 μM ZnSO$_4$. Decorin proteoglycan (DcnPg) (0.4 μM) derived from cultured mammalian cells (FIG. 2A), or 2 μM decorin core protein (Dcn) expressed by vaccinia virus-infected mammalian cell line CHO745 that lacks xylosyl transferase activity (FIG. 2B) were also added to the medium. Time course of fibrin clotting was monitored spectroscopically after adding thrombin to a final concentration of 0.25 U/ml. This example demonstrates that Zn$^{2+}$ enhances fibrin clotting in the presence or absence of decorin proteoglycan or decorin core protein. The results also show that contacting fibrinogen with a sufficient concentration of decorin proteoglycan in the presence of physiological levels of zinc will inhibit fibrin (ogen) clotting in vitro.

EXAMPLE 3

Comparison of The Inhibitory Action of Decorin Proteoglycan And Heparin Cofactor II Towards Thrombin Cleavage of Fibrinogen Two μM fibrinogen was pre-incubated in HBS, 0.1% CHAPS, 20 μM ZnSO$_4$ with or without 2.5 U/ml heparin cofactor II (HCII); 0.4 μM decorin proteoglycan (DcnPg) expressed by mammalian cells capable of producing dermatan sulfate; 0.4 μM decorin proteoglycan plus 2.5 U/ml HCII; 0.4 μM chondroitin sulfate B (CSB) plus 2.5 U/ml HCII; 0.4 μM chondroitin sulfate A (CSA) plus 2.5 U/ml HCII (FIG. 3A); or 2.5 U/ml hirudin or 0.6 mM chromogenic thrombin substrate S-2238 (FIG. 3B). After adding thrombin to 0.25 U/ml, the progress of each reaction was traced by the absorbance at 405 nm which detects fibrin clotting (FIG. 3A) or p-nitroaniline release (FIG. 3B).

As shown in FIG. 3A, the combination of decorin proteoglycan with heparin cofactor II inhibits clotting more potently than either compound alone and also more potently than dermatan sulfate with heparin cofactor II. According to FIG. 3B, the polysaccharide component of decorin may not be rich in dermatan sulfate since the effect of decorin on heparin cofactor II inhibition of thrombin was minimal in a system where thrombin cleaves a chromogenic substrate. These findings show that the potency of decorin proteoglycan derives from the ability of the decorin core protein to bind fibrinogen and target the antithrombotic polysaccharide and perhaps heparin cofactor II to the site of thrombin action.

EXAMPLE 4

Concentration-Dependent Effects of Decorin Core Protein On Fibrin Clotting

Two μM fibrinogen was pre-incubated for 1.5 hours at ambient temperature in HBS, 0.1% CHAPS, 20 uM ZnCl$_2$, 5 mM CaCl$_2$, 5 mM EACA, pH 7.4 with or without increasing concentrations of decorin core protein expressed by CHO745 cells, a recombinant vaccinia virus-infected mutant CHO cell line lacking xylosyl-transferase activity. All subsequent steps were performed as described under Example 1.

The results show that contacting fibrinogen with increasing concentrations of decorin core protein prior to introducing thrombin slows the progress of fibrin(ogen) clotting and alters the structure of the clot in a concentration-dependent fashion (FIG. 4). The progress of clotting and final clot structure are described quantitatively as the rate and final absorbance values, respectively (Table 2).

TABLE 2

Thrombin-Induced Clotting of Buffered Fibrin(ogen) in the Absence or Presence of Decorin Core Protein

| [Decorin] μM | Rate$^a$ (mAbs/min) | Final Abs$^a$ (405 nm) |
| --- | --- | --- |
| 0   | 90.0 ± 4.3 | 0.206 ± 0.005 |
| 0.2 | 61.8 ± 4.3 | 0.160 ± 0.004 |
|     | (p < 0.01) | (p < 0.01) |
| 0.4 | 55.0 ± 3.0 | 0.145 ± 0.003 |
|     | (p < 0.002) | (p < 0.002) |
| 1.0 | 38.8 ± 4.3 | 0.120 ± 0.002 |
|     | (p < 0.0003) | (p < 0.0003) |
| 2.0 | 34.5 ± 2.5 | 0.113 ± 0.001 |
|     | (p < 0.0006) | (p < 0.0006) |

$^a$Values in each column represent the mean (n = 4).
p values indicate a statistically significant difference when compared to fibrinogen alone.

EXAMPLE 5

Decorin Core Protein Alters The Structure of Fibrin(ogen) Clot

Fibrin(ogen) clotting was induced by the addition of thrombin (final concentration 0.4 U/ml) to fibrinogen pre-incubated in the absence or presence of decorin core protein under the solution conditions described in Example 4. Scanning electron microscopy was utilized to obtain images of clots formed from 1.2 μM fibrin(ogen) alone (FIG. 5A) or in the presence of 0.24 μM (FIG. 5B) or 1.2 μM (FIG. 5C) decorin core protein. The results show that contacting fibrinogen with decorin core protein prior to introducing thrombin results in an altered fibrin(ogen) clot structure. Fibrin(ogen) fibril growth is attenuated by decorin in a concentration-dependent fashion.

EXAMPLE 6

Concentration-Dependent Effects of A 45 Amino Acid Residue Peptide Mimetic of The N-Terminal Region of Decorin Core Protein On Fibrin Clotting Clotting assays were performed in the absence or presence of a 45 amino acid residue peptide mimetic of the N-terminal region of decorin core protein (DcnNTD). Assay conditions were the same as described above. The results show that contacting fibrinogen with increasing concentrations of the 45 amino acid residue peptide mimetic of the N-terminal region of decorin core protein prior to introducing thrombin slows the progress of fibrin(ogen) clotting and alters the structure of the clot in a concentration-dependent fashion (FIG. 6). The progress of clotting and final clot structure are described quantitatively as the rate and final absorbance values, respectively (Table 3).

TABLE 3

Thrombin-Induced Clotting of Buffered Fibrin(ogen) in the Absence or Presence of Decorin Peptide (DcnNTD)

| [DcnNTD] μM | Rate[a] (mAbs/min) | Final Abs[a] (405 nm) |
| --- | --- | --- |
| 0 | 110 ± 6 | 0.24 ± 0.01 |
| 2.0 | 102 ± 3 | 0.23 ± 0.01 |
| 6.0 | 91 ± 3 | 0.22 ± 0.01 |
|  |  | ($p < 0.03$) |
| 12 | 80 ± 2 | 0.213 ± 0.002 |
|  | ($p < 0.05$) | ($p < 0.01$) |
| 30 | 70 ± 3 | 0.197 ± 0.005 |
|  | ($p < 0.002$) | ($p < 0.01$) |

[a]Values in a column represent the mean (n = 4).
p values indicate a statistically significant difference when compared to fibrinogen alone.

The following references were cited herein:

Dugan et al., J. Biol. Chem. 278:13655–13662 (2003).
Yang et al., J. Biol. Chem. 274:12454–12460 (1999).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A recombinant anticoagulating and antithrombotic decorin proteoglycan with the sequence of SEQ ID NO: 2 linked to a galactosaminoglycan polysaccharide.

2. The recombinant decorin proteoglycan of claim 1, wherein said galactosaminoglycan polysaccharide is covalently linked thereto.

3. The recombinant decorin proteoglycan of claim 1, wherein said proteoglycan comprises a fibrinogen-binding domain.

4. The recombinant decorin proteoglycan of claim 1, wherein said proteoglycan is chemically derivatized.

5. The recombinant decorin proteoglycan of claim 1, wherein said galactosaminoglycan polysaccharide comprises heparin, heparan sulfate, chondroitin sulfate or dermatan sulfate or a combination thereof.

6. A pharmaceutical composition comprising the recombinant decorin proteoglycan of claim 1 and a pharmaceutically acceptable carrier.

7. A kit for inhibiting fibrin clot formation, comprising the composition of claim 6.

8. The kit of claim 7, further comprising:
an anticoagulating agent, wherein said anticoagulating agent is heparin cofactor II, chondroitin sulfate or dermatan sulfate or a combination thereof.

* * * * *

SEQUENCE LISTING

```
<160> NUMBER OF SEQ ID NOS: 2

<210> SEQ ID NO 1
<211> LENGTH: 41
<212> TYPE: PRT
<213> ORGANISM: Unknown
<220> FEATURE:
<221> NAME/KEY: DOMAIN
<223> OTHER INFORMATION: N-terminal region of decorin

<400> SEQUENCE: 1

Asp Glu Ala Ser Gly Ile Ile Pro Tyr Asp Pro Asp Asn Pro Leu
                 5                  10                  15

Ile Ser Met Cys Pro Tyr Arg Cys Gln Cys His Leu Arg Val Val
                20                  25                  30

Gln Cys Ser Asp Leu Gly Leu Asp Lys Val Pro
                35                  40

<210> SEQ ID NO 2
<211> LENGTH: 45
<212> TYPE: PRT
<213> ORGANISM: Artificial Sequence
<220> FEATURE:
<221> NAME/KEY: DOMAIN
<223> OTHER INFORMATION: recombinant N-terminal decorin peptide

<400> SEQUENCE: 2

Gly Ser Asn Gly Asp Glu Ala Ser Gly Ile Ile Pro Tyr Asp Pro
                 5                  10                  15

Asp Asn Pro Leu Ile Ser Met Cys Pro Tyr Arg Cys Gln Cys His
                20                  25                  30

Leu Arg Val Val Gln Cys Ser Asp Leu Gly Leu Asp Lys Val Pro
                35                  40                  45
```